United States Patent
Stähler et al.

(10) Patent No.: US 7,097,974 B1
(45) Date of Patent: *Aug. 29, 2006

(54) SUPPORT FOR A METHOD FOR DETERMINING AN ANALYTE AND A METHOD FOR PRODUCING THE SUPPORT

(75) Inventors: Cord F. Stähler, Weinheim (DE); Peer F. Stähler, Mannheim (DE); Manfred Müller, München (DE); Fritz Stähler, Weinheim (DE); Hans Lindner, Stuttgart (DE)

(73) Assignee: febit biotech GmbH, Heidelberg (DE)

( * ) Notice: Subject to any disclaimer, the term of this patent is extended or adjusted under 35 U.S.C. 154(b) by 0 days.

This patent is subject to a terminal disclaimer.

(21) Appl. No.: 09/763,914

(22) PCT Filed: Aug. 27, 1999

(86) PCT No.: PCT/EP99/06317

§ 371 (c)(1),
(2), (4) Date: May 11, 2001

(87) PCT Pub. No.: WO00/13018

PCT Pub. Date: Mar. 9, 2000

(30) Foreign Application Priority Data

| Aug. 28, 1998 | (DE) | 198 39 254 |
| Aug. 28, 1998 | (DE) | 198 39 255 |
| Aug. 28, 1998 | (DE) | 198 39 256 |
| Feb. 19, 1999 | (DE) | 199 07 080 |
| May 27, 1999 | (DE) | 199 24 327 |

(51) Int. Cl.
*C12Q 1/68* (2006.01)
*G01N 33/543* (2006.01)
*G01N 33/552* (2006.01)

(52) U.S. Cl. ............ 435/6; 435/970; 435/973; 435/DIG. 46; 435/DIG. 49; 436/518; 436/527; 536/25.3; 536/25.31

(58) Field of Classification Search ........ 435/6, 435/970, 973; 436/89, 518, 527, 528; 536/25.1, 536/25.3, 25.31
See application file for complete search history.

(56) References Cited

U.S. PATENT DOCUMENTS

| 5,143,854 A | 9/1992 | Pirrung et al. |
| 5,247,180 A | 9/1993 | Mitcham et al. |
| 5,318,679 A | 6/1994 | Nishioka |
| 5,384,464 A | 1/1995 | De Fornel et al. |
| 5,405,783 A | 4/1995 | Pirrung et al. |
| 5,424,186 A | 6/1995 | Fodor et al. |
| 5,474,796 A | 12/1995 | Brennan |
| 5,545,531 A | 8/1996 | Rava et al. ............ 435/6 |
| 5,547,839 A | 8/1996 | Dower et al. |
| 5,653,939 A | 8/1997 | Hollis et al. |
| 5,677,195 A | 10/1997 | Winkler et al. |
| 5,723,320 A | 3/1998 | Dehlinger ............ 435/9.1 |
| 5,728,251 A | 3/1998 | Check, III |
| 5,741,411 A * | 4/1998 | Yeung et al. ............ 204/452 |
| 5,755,942 A | 5/1998 | Zanzucchi et al. |
| 5,789,162 A | 8/1998 | Dower et al. |
| 5,807,525 A | 9/1998 | Allen et al. |
| 5,812,272 A | 9/1998 | King et al. |
| 5,843,655 A | 12/1998 | McGall |
| 5,846,708 A | 12/1998 | Hollis et al. |
| 5,849,486 A | 12/1998 | Heller et al. |
| 5,952,172 A | 9/1999 | Meade et al. |
| 5,968,745 A | 10/1999 | Thorp et al. |
| 6,001,311 A | 12/1999 | Brennan |
| 6,024,925 A | 2/2000 | Little et al. |
| 6,066,448 A | 5/2000 | Wohlstadter et al. |
| 6,136,269 A | 10/2000 | Winkler et al. |
| 6,271,957 B1 | 8/2001 | Quate et al. |
| 6,295,153 B1 | 9/2001 | Garner |
| 6,375,903 B1 | 4/2002 | Cerrina et al. |
| 6,420,169 B1 | 7/2002 | Read et al. |
| 6,582,917 B1 | 6/2003 | Beier |
| 6,586,211 B1 * | 7/2003 | Stahler et al. ............ 435/91.1 |
| 2002/0160427 A1 | 10/2002 | Beier et al. |
| 2003/0175781 A1 | 9/2003 | Beier |
| 2003/0198948 A1 | 10/2003 | Stähler et at. |
| 2004/0043509 A1 | 3/2004 | Stähler et al. |
| 2004/0175734 A1 | 9/2004 | Stähler et al. |

(Continued)

FOREIGN PATENT DOCUMENTS

CA 2345157 A1 11/1999

(Continued)

OTHER PUBLICATIONS

J.D. Hoheisel, "Oligomer-chip technology", Trends in Biotechnology, vol. 15, No. 11, Nov. 1997, pp. 465-469.

(Continued)

*Primary Examiner*—Padmashri Ponnaluri
*Assistant Examiner*—My-Chau T. Tran
(74) *Attorney, Agent, or Firm*—Rothwell, Figg, Ernst & Manbeck, P.C.

(57) ABSTRACT

A method for producing a support for determining analytes. The method comprises the steps of (a) providing a support comprising at least one channel, comprising a conduit having an intake and an outlet for passing fluid from the intake to the outlet, in the support body, (b) passing liquid with building blocks for synthesizing polymeric receptors through the channel or channels of the support body, (c) site- and/or time-specifically immobilizing the receptor building blocks in each case on predetermined positions in the channel or channels by illumination and (d) repeating steps (b) and (c) until the required receptors have been synthesized in each case on the predetermined positions.

11 Claims, 4 Drawing Sheets

U.S. PATENT DOCUMENTS

2005/0037407 A1  2/2005  Beier et al.

FOREIGN PATENT DOCUMENTS

| | | |
|---|---|---|
| CA | 2371938 | 1/2000 |
| DE | 8309254.4 | 1/1985 |
| DE | 69012119 T2 | 3/1992 |
| DE | 04241871 A1 | 6/1994 |
| DE | 69217497 T2 | 7/1994 |
| DE | 04325724 A1 | 2/1995 |
| DE | 69328693 T2 | 7/1996 |
| DE | 69218572 | 11/1997 |
| DE | 69032277 T2 | 4/1998 |
| DE | 19731479 A1 | 6/1998 |
| DE | 69130251 T2 | 9/1998 |
| DE | 19901761 A1 | 7/1999 |
| DE | 19823876 A1 | 12/1999 |
| DE | 19940751 A1 | 3/2000 |
| DE | 19842164 | 4/2000 |
| DE | 19921940 A1 | 6/2000 |
| DE | 19926457 A1 | 7/2000 |
| DE | 199 10 392 | 9/2000 |
| EP | 0430248 A2 | 6/1991 |
| EP | 0493137 | 7/1992 |
| EP | 0549993 A1 | 7/1993 |
| EP | 0671626 A1 | 9/1995 |
| EP | 0955085 A2 | 11/1999 |
| JP | 9288080 | 11/1997 |
| WO | WO 91/18276 A1 | 11/1991 |
| WO | WO 92/10092 * | 6/1992 |
| WO | WO 93/20230 A1 | 10/1993 |
| WO | WO 93/22678 | 11/1993 |
| WO | 95 01559 | 1/1995 |
| WO | WO 95/12808 A1 | 5/1995 |
| WO | 96 10747 | 4/1996 |
| WO | WO 96/33971 A1 | 10/1996 |
| WO | WO 96/40712 A1 | 12/1996 |
| WO | WO 97/06468 A2 | 2/1997 |
| WO | WO 97/12030 A1 | 4/1997 |
| WO | 97 19749 | 6/1997 |
| WO | WO 97/39151 | 10/1997 |
| WO | WO 97/41425 A1 | 11/1997 |
| WO | WO 98/03683 A1 | 1/1998 |
| WO | WO 98/08085 | 2/1998 |
| WO | 98 13683 | 4/1998 |
| WO | WO 98/30893 A1 | 7/1998 |
| WO | WO 98/51819 A1 | 11/1998 |
| WO | WO 98/53093 | 11/1998 |
| WO | WO 98/58293 A2 | 12/1998 |
| WO | WO 99/09042 | 2/1999 |
| WO | WO 99/19510 A1 | 4/1999 |
| WO | WO 99/27140 A1 | 6/1999 |
| WO | WO 99/31275 A1 | 6/1999 |
| WO | WO 99/37819 A2 | 7/1999 |
| WO | WO 99/39817 A1 | 8/1999 |
| WO | WO 99/41007 | 8/1999 |
| WO | WO 99/42813 | 8/1999 |
| WO | WO 99/60156 | 11/1999 |
| WO | WO 99/60170 | 11/1999 |
| WO | WO 99/63385 | 12/1999 |
| WO | WO 00/11473 A1 | 3/2000 |
| WO | WO 00/13017 | 3/2000 |
| WO | WO 00/13018 | 3/2000 |
| WO | WO 02/32567 A1 | 4/2002 |

OTHER PUBLICATIONS

Neff, John A., "Two-Dimensional Spatial Light Modulators: A Tutorial", Proceedings of the IEEE, vol. 78, No. 5, May 1990, pp. 826-854.

Berstch et al., "Study of the Spatial Resolution of a New 3D Micorfabrication Process: the Microstereophotolithography Using a Dynamic Mask-Generator Technique," Journal of Photochemistry and Photobiology A: Chemistry, 107:275-281, 1997.

Davidson Mark, "A Microlens Direct-Write Concept for Lithography," SPIE, 3048:346-355.

Hoheisel, J.D., "Oligomer-Chip Technology," Trends in Biotechnology, 15(11):465-469, 1997 (missing p. 469).

Singh-Gasson et al., "Maskless Fabrication of Light-Directed Oligonucleotide Microarrays Using a Digital Micromirror Array," Nature Biotechnology, 17:974-978, 1999.

Retrieved from the Internet: "Digital Optical Chemistry System," http://innovation.swmed.edu/research/instrumentation/higher_pages.

Hanley, et al. "Charge Transfer Device in Analytical Instrumentation," Anal. Chem. 68:A661-A667, 1996.

Johnson et al., "Micromirror arrays perform photolithography step,"EETTIMES.com, (1999), 2 pgs.

Kirschner, et al., "Minaturisiete NIR-Diodenarray-Spektrometer," GIT Labor-Fachzeitschrift 402-404, 1998, (with English Abstract).

Villemoes et al., "A Computerized Peptide Synthesizer with Feed back Control," Acta Chemica Scand. B 32:703-713, 1978.

von Buren et al., "Branched Oligodeoxynucleotides: Automated Synthesis and Triple Helical Hybridization Studies," Tetrahedron Lett. 51(31):8491-8506, 1995.

German Search Report of Aug. 9, 1999, from DE 19839254.0 (with English translation).

German Search Report of Apr. 17, 2000, from DE 19940752.5 (with English translation).

* cited by examiner

SUPPORT FOR A METHOD FOR DETERMINING AN ANALYTE AND A METHOD FOR PRODUCING THE SUPPORT

1. AREA OF APPLICATION OF THE INVENTION

1.1 Background

The precise detection of biologically relevant molecules in defined investigation material is of outstanding importance for basic research in the biosciences and for medical diagnostics, and some other disciplines. In this connection, the genetic information is present in the form of an enormous variety of different nucleic acid sequences, the DNA. Realization of this information leads via the production of transcripts of the DNA in RNA usually to the synthesis of proteins, which in turn are frequently involved in biochemical reactions.

The detection of particular nucleic acids and the determination of the sequence of the four bases in the chain of nucleotides, which is generally referred to as sequencing, provides valuable data for research and applied medicine. In medicine, it has been possible to a greatly increasing extent to develop, through in vitro diagnosis (IVD) instruments for determining important parameters of patients, and to provide the treating physician therewith. Without this instrument, it would be impossible to diagnose many diseases at a sufficiently early time. Genetic analysis has become established here as an important new method, for example for infectious diseases such as HIV and HBV, genetic predisposition for certain types of cancer or other diseases, forensic medicine and a large number of other areas of application. It has been possible with close interlinkage of fundamental research and clinical research to trace back and elucidate the molecular causes and (pathological) relationships of some disease states as far as the level of the genetic information. This development is, however, still in its infancy, and much more intensive efforts are needed in particular for conversion into therapeutic strategies. Overall, the genomic sciences and the nucleic acid analytical techniques associated therewith have made enormous contributions both to the understanding of the molecular bases of life and to explaining very complex disease states and pathological processes.

Further development in medical care will be burdened by the explosion in costs associated with correspondingly elaborate methods. In this connection it is necessary not only to push for implementation of the possibilities for diagnostic and therapeutic benefits, but also to promote integration into a health system which is capable of bearing the load and can be financed.

Use of corresponding technologies in research can likewise take place on a broad scope and in the academic sector only if the costs associated therewith are reduced.

1.2 Need

The development of the genomic and proteomic sciences and the deciphering of the hereditary material are still at an early stage, as is the realization of the diagnostic potential of a genetic or gene-manipulative analysis. The methods established to date are usually labor-intensive and relatively inefficient, which influences the costs and capacity for example for gaining information. The most important innovation is the development of so-called oligonucleotide arrays in which a very large number of relatively short oligonucleotides of defined sequence are coupled to a solid matrix (usually silicon) and are thus made available for parallel hybridization of complementary sequences in the material to be investigated. The elaborate production and the high cost do not, however, allow marketing as a mass-produced item at present.

1.3 Fields of Application

It is intended to employ distinctly cost-reduced systems to make routine use possible for in vitro diagnostics and clinical diagnostics, for example of infectious diseases (HIV, HBV etc.) and their subtypes, for oncology (early tumor diagnosis, tumor classification, for example type and status), and for determination of a genetic predisposition.

It is desirable for fundamental biological research, especially genomics, to encompass a very large number of measurement points in the investigated system, for example all expressed genes. This results in an enormous gain in knowledge in fundamental biological research (developmental biology, stem cell culture, tissue engineering, transplantation medicine, regeneration), which will also lead to important break-throughs in biomedicine and corresponding applications.

As has been shown for the use of DNA chips (Science 280: 1077–1082), it is possible to make a distinction between point mutations in the base sequence through corresponding biochemical conditions of hybridization. The system described therein thus makes extensive screening possible, which can be employed for forensic purposes, for example for convicting those guilty of crimes or for detecting family relationships.

This invention also enables the fast and cost-effective analysis of foodstuffs, for example for the presence of particular genes from pathogenic organisms or from genetically manipulated organisms.

The screening of medicinal products is likewise of great importance. The production of, for example, blood products is still associated with large expenditure ins respect of the safety measures needed for purity. Screening which is efficient in terms of both time and costs for such samples is made possible by this invention in order, for example, to prevent contamination with infectious material (HIV, HBV, HCV etc.).

2. PRIOR ART

Biochips are miniaturized hybrid functional elements with biological and technical components, for example biomaterials which are immobilized on the surface of a support and which can act as specific interaction partners (for example DNA oligonucleotides), and a silicon matrix. These functional elements are usually arrange in rows and columns, in which case they are called biochip arrays. Since thousands of biochemical functional elements can be arranged on the biochip, they must be produced by microengineering methods.

Enormous funds are being used, especially in the USA, to promote the development of miniaturized biochips. The most important companies active in this field are listed below:

Affymetrix, Beckman Instruments, Blue Chip Biosystems, Caliper Technologies, Cura-Gen, Genometrix, Gene Trace Systems, Hyseq, Incyte Pharmaceuticals, Molecular Tool, Nanogen, Pharmacia, Synteni, Third Wave Technologies, Vysis.

Biochips disclosed to date can be classified by the following criteria:
Detection principle:
Chromatographic methods
Interaction of analytes with solid phase, usually immobilized interaction partners (for example hybridization of nucleic acids on DNA oligonucleotides).
Detection methods (optical, electrical).
Marker-based detection methods (for example absorption, fluorescence or luminescence) or marker-free detection methods (generation of light to detect the reaction).
Assignment of the analyte to its support [solid phase] (array, with more than one immobilized interaction partner per support or single, with only one immobilized interaction partner per support).
Production method (for example photoactivated synthesis of oligonucleotides directly on the biochip, spot completely synthesized oligonucleotides, coat beads or tubes).
Types of support (glass chips, plastic chips, microtiter plates, tubes or beads).
Presentation for detection (serially, in parallel).
Optical detection (serially in a scanner or in parallel with a CCD camera).

Among the firms listed, only Affymetrix uses the principle of photolithography for generation of high density DNA arrays on a planar surface, whereby it has made by far the greatest advances in the parallelization of oligo sequences detection.

GeneChip from Affymetrix Inc., Santa Clara, Calif.:

Production takes place by in situ synthesis of DNA oligonucleotides on planar chips in high density (July 98: up to 64 000 different oligos on 1 cm$^2$). The production method is based on photolithography, which is used and has been optimized in the semiconductor industry and which entails use of photoactivatable binding of oligos to the chip surface as well as to oligos already present. Production takes several hours due to the large number or process steps. Detection takes place by serial optical detection of the planar chip in a fluorescence scanner. Hybridization of the sample on a chip takes about 1.5 hours. First products (sequencing chip for tumor marker p53 exons 2–11, breast cancer gene BRCA1 exon 11, HIV GeneChip) are already commercially available. The costs at present are in the region of several hundred dollars for one GeneChip, additionally a detection unit is also required.

Further relevant prior art are WO91/18276, EP-A-0 671 626 and EP-A-0 430 248.

3. SUMMARY OF THE INVENTION AND OBJECT ACHIEVED THEREBY

The invention relates to a method for producing a support for determining analytes, comprising the steps of
(a) providing a support body comprising at least one channel,
(b) passing liquid with building blocks for synthesizing polymeric receptors through the channel or channels of the support body,
(c) site- or/and time-specifically immobilizing the receptor building blocks in each case on predetermined positions or regions in the channel or channels and
(d) repeating steps (b) and (c) until the required receptors have been synthesized in each case on the predetermined positions or regions.

In preferred refinements of this method, the support is a solid phase which can be or is charged with biologically or chemically functional materials or receptors (probes) or building blocks thereof. In this embodiment of the invention, the support has a surface which is provided with depressions, for example at least one channel and particularly preferably with a large number of channels. The channels are preferably microchannels with a cross section of, for example, 10 to 1 000 μm. The channels may be—depending on the surface properties—capillary channels, but also channels without capillary action (for example because of Teflon coating). The support is preferably optically transparent at least partly in the region of the positions or regions to be charged with receptors. The regions of the support which are to be charged with receptors are preferably chemically and physically identical to one another, i.e. they have essentially identical surface characteristics.

The invention further relates to a method for integrated synthesis and analyte determination on a support, comprising the steps of
(a) providing a support body,
(b) passing a liquid with, present therein, receptors or building blocks for synthesizing polymeric receptors over the support,
(c) site- or/and time-specifically immobilizing the receptors or receptor building blocks in each case on predetermined positions or regions on the support,
(d) where appropriate, repeating steps (b) and (c) until the required receptors have been synthesized in each case on the predetermined positions or regions on the support,
(e) bringing the support into contact with a sample containing analytes to be determined and
(f) determining the analytes via their binding to the receptors immobilized on the support.

The invention also relates to preferred refinements of this method. It is also possible to use planar supports in this embodiment.

The invention also relates to a support for determining analytes comprising at least one channel and preferably a large number of channels, in particular capillary channels, whereby a large number of different receptors are immobilized in the channels. The support is preferably optically transparent at least in the region of the regions to be charged with receptors.

The invention further relates to a reagent kit comprising a support as described above, and building blocks for synthesizing polymeric receptors on the support. The reagent kit may additionally comprise reaction liquids for synthesizing the receptors on the support.

The invention also relates to an apparatus for integrated synthesis and analyte determination on a support comprising a programmable light source matrix, a detector matrix, a support arranged between light source matrix and detector matrix, and means for supplying fluids into the support and for discharging fluids from the support. The programmable light source or illumination matrix may be a reflection matrix, a light valve matrix, for example an LCD matrix or a self-emitting illumination matrix.

Finally, the invention also relates to the use of the claimed method, support, reagent kit and the claimed apparatus for determining an analyte in a sample.

One embodiment of the present invention is represented by a method and system for cyclic integrated synthesis and analysis, which is to be referred to as the ISA system. Direct coupling, which is preferred according to the invention, of synthesis and analysis makes high throughput determination of analyzes, which is a distinct improvement over the prior art, possible in a cyclic method. It is possible in this connection for the substances to be analyzed to be, for example, in the form of segments or fragments of a larger molecule chain.

In a preferred embodiment of the invention, a direct logical linkage is provided between the results of the analysis of a first support and the synthesis of the support which is to be subsequently produced, thereby making it possible to transfer the information gained in a preceding cycle to a subsequent cycle. In this way there is stepwise development of learning of the analytical system.

Said cyclic sequence of synthesis, sequence comparison, analysis of the comparative results and renewed synthesis of receptors on the support can be repeated as often as desired—until a desired termination criterion, which can be chosen as required—is reached.

The feedback, and the learning process associated therewith, from the preceding cycle makes the method of the invention and the apparatus also suitable for research on very large and complex analyte molecule chains, for example for sequencing in individual genomes, such as the human genome. The expenditure of time in this case is improved compared with the prior art by at least one hundred-fold, more probably by one thousand-fold and potentially by 10 000-fold.

The method can be employed for "new sequencing" of unknown nucleic acid sequences (DNA, cDNA, RNA) including their spatial arrangement, or mapping. It is possible with this procedure to produce an individual gene profile of each individual and each species, whether by sequencing parts of the genome or of the whole genome.

The method can additionally be employed for "resequencing" of nucleic acid sequences, i.e. for comparing previously known sequences (represented in the form of the receptor probes) with unknown sequences in the sample to be investigated. The known sequences are selected appropriately for the problem and specifically for this purpose.

The described resequencing allows the user to generate individual polymeric receptors on site on the support of the invention starting from a neutral support and subsequently to immediately carry out an analysis of the sample to be investigated. This possibility results in a maximum diversity of variants of the receptors with a minimal space requirement.

It is possible by combining new sequencing and resequencing to adapt diagnostic tests or medicines to the needs of an individual at short notice.

It is possible with exceptional flexibility to analyze expression patterns as a further important area of application. The corresponding receptors or polymer probes for this purpose are usually, selected on the basis of known sequences. The use of the method for determining gene expression can also take place in the context of high throughput screening.

In addition, different approaches to screening methods and the setting up and analysis of substance libraries are conceivable with various naturally occurring and artificial receptor probes. This may take place, for example, in connection with the search for and the characterization of pharmacologically active substances.

The fields of application of the method of the invention and the apparatus of the invention for cyclically integrated synthesis and determination of analytes are wide-ranging and extend in principle to all analytical applications such as gas chromatography, thin-layer chromatography, gel electrophoresis, capillary electrophoresis, mass spectrometry etc. The same applies in principle to all applications of highly parallel solid-phase analysis.

There is no longer any need at all to store complex polymeric receptors ready for use. In addition, there is no physical restriction on the number and selection of the receptors. The required number of receptors can be distributed over a plurality of reaction supports or a plurality of cycles in a reaction support, because the individual receptors are subject to no site specifications for logical evaluation of the comparative results.

The present invention relates to a novel "support" as basis for the use of a preferably light-controlled synthesis of individual bases (G, A, C and T) or oligonucleotides (base sequences) to form a highly parallel, planar and dense arrangement (array) of these oligonucleotides in a solid support matrix (chip).

The novel biochip, the "optofluidic microprocessor", comprises a structure of microchannels, preferably capillaries, in an at least partially transparent and preferably flat body. On synthesis or immobilization of receptors, the liquid starting materials are passed through the channels in the support and bind, locally activated, to the channel walls. This creates the technical requirements for a rapid, efficient and thus cost-effective production, which will make wide use of these supports possible. The density and parallelity are of the same order of magnitude as for competing techniques, with several hundred thousand defined oligonucleotides on a support. The advantage of the novel technique is the more favorable physicochemical properties of the flow and wetting processes in the channels compared with a uniform surface.

Production of the chips consists of producing a support body, which is preferably provided with microchannels, from a suitable, light-transmitting material, and of the biochemical coating process, preferably on the walls of the individual microchannels, so that subsequent synthesis of the polymeric receptors, for example oligonucleotides, in the channels is possible. This entails site-specific attachment of individual receptor building blocks, oligomeric synthons (for example di-, tri-, tetra- or pentanucleotides) or whole base sequences (oligos) in the individual channels in the support by means of photoactivation by a suitable light source. This results in a large number of receptor-charged regions (specific binding or hybridization sites) in each channel, and each region serves, because of its individual receptor-sequence combination, for the binding and subsequent detection of a specific analyte, for example a DNA fragment. The regions are separated from one another in one dimension of the planar support by the walls of the channels, and with photoactivated binding a corresponding free space is left between two adjacent regions along the individual channels. The result is a highly parallel, highly integrated array of specific receptors. Because of the possibility of multiplexing oligosequences and parallel channels (for details, see section 5), it is possible to reduce the production times to ¼ on use of single bases, ⅛ with dinucleotides and to ¹⁄₁₆ with trinucleotides by appropriate multiplexing of the oligos (starting materials) and of the channels to be wetted. This also makes flexible adaptation to customers' requirements, the "tailored" biochip, possible. This systematic speeding up is not possible in planar systems (planar chips).

For the analysis, the investigational material (for example DNA, RNA in solution) is passed through the channels and has the opportunity to bind to the receptors, for example by hybridization onto complementary strands, if these are present. It is preferred to use high-resolution, parallel CCD chips for detection and evaluation of the particular analyte binding, for example a DNA hybridization. The binding of the analyte to the immobilized receptor is [lacuna] by suitable signal-emitting groups known from the prior art, for example light-emitting groups. However, novel detection methods can also be applied. For detection it is possible to do without optically imaging lens systems if the size of the channels is chosen so that each measurement point covers a sufficient number of pixel elements of the detector, for example of a CCD chip. This direct usage (no optical system) of highly parallel CCD matrix chips with a large number (currently 16 million pixels per 1 $cm^2$; research status: 80 million pixels per 1 $cm^2$) of pixels (optical sensors) makes it possible to detect a large number of light signals in parallel (see BioScanner from Genometrix). Therefore it is attempted even for the detection unit to have recourse to a high-tech product fabricated in large numbers and at low cost in place of costly optical arrangements.

The invention thus covers the essential requirements for DNA analysis, namely simultaneous determination of a large number of DNA sequences (achieved by highly integrated, miniaturized supports and high-resolution optical detection), provision of cost-effective tests (multiplexing in production, low-cost disposable supports, for example injection-molded, rapid synthesis during production), rapid procedure for the analysis due to small volumes and favorable wetting processes, reduction in starting materials through the flow geometry of the support etc., rapid evaluation (achieved by parallel optical evaluation in planar arrangements [DNA chip array]), a cost-effective analytical system (achieved by dispensing with costly, microsystem and optical components) and ensuring quality both during production and during analysis (achieved by defined flow processes in the support).

The use of photoactivation of chemical reactions in the area of the support synthesis leads, in particular in combination with the technology platform of the optofluidic microprocessor together with a programmable light source matrix, to the breakthrough, because this makes it possible to reduce the production costs for a single support while, at the same time, improving the quality, by a factor of 10–100. In this way, a cost-effective, massively parallel, highly integrated and, at the same time, easily miniaturizable and automatable DNA chip technology is made available for the first time.

Despite the complex data evaluation, only a minimum of different hardware components is required because the support bodies which need to be changed either for each cycle or only when worn are initially all—before the start of the receptor synthesis—identical. All individuality results only from the specific receptor synthesis and from the information obtained stepwise by the analysis which, after the synthesis/analysis cycle, is converted back into information, so that the individuality, i.e. the characterizing features of the biological/chemical material, are once again present only in the form of electronic data.

4. MAIN FEATURES OF THE MODE OF ACHIEVEMENT

The mode of achievement in principle in this system is based on stepwise biochemical synthesis of receptors on the surfaces of a large number of channel walls on a support. These channels are arranged on the support, for example a small planar chip. The synthesis takes place with the appropriate bases or multi-base oligonucleotides (base sequences) by photoactivated site-specific binding. The wetting of these specifically "labeled" channels with the DNA analytes to be investigated and the subsequent detection of the binding reaction via suitable signal-emitting groups concludes a cycle of the method.

4.1 Microstructure as Support Matrix

The support synthesis comprises the provision of the support body, which preferably consists of a suitable, light-transmitting material, and the biochemical generation of receptors on the walls of the individual channels. The specific synthesis of the receptors can take place either directly during production of the support body or not until used.

Various materials (for example glass, silicon, ceramic, metal or plastic) can be used for the support bodies. It is important that the walls of the channels satisfactorily transmit both the excitation waves for the photoactivated synthesis and the light waves (where appropriate excitation and reaction signal) for the subsequent detection (analysis). Depending on which material is employed, the walls of the channels must be coated with a reactive material so that the receptors or receptor building blocks can bind to the surface.

The geometry of the supports corresponds, for example, to a "check card" and the size of the area covered by the channels is determined by the CCD chip used for detection. Various methods can be employed to produce the channels in the support. Account must be taken on the influence of the cross-sectional geometry of the channels, which has a great influence on the resulting hydrodynamic forces and the possibility of cleaning the channels. Methods which can be used for production are, for example, laser, milling, etching techniques or injection molding.

The following aspects must be taken into account in the arrangement of the channels in the plane: if a large number of parallel channels is used, it is possible to minimize the synthesis times, but the wetting or filling of the individual channel is correspondingly complex. If, at the other extreme, there is only a single long channel, the synthesis is correspondingly slow because the multiplexing of channels to bases or whole oligos cannot be used, and all processes can take place only serially one after the other. The advantage of only one channel is for the analysis, where the sample flows past each measurement point in all the channels.

4.2 Synthesis Cycle in the Support

The positions (reaction regions) intended for coating with receptors in a support body are filled with one or more fluids through channels from containers via feed lines, valves and fittings. It is possible with the aid of a light emission/detection unit which is disclosed in German patent application 198 39 254.0 and which is preferably a programmable light source or illumination matrix, as described in German patent application 199 07 080.6, to illuminate selected positions or regions on the support and, in this way, control the individual synthesis of receptors, the support being in this connection an optofluidic microprocessor. In place of illumination, the selected reaction regions can also undergo individual fluidic activation. After completion of the reaction, the reaction regions are rinsed and refilled, after which another activation cycle follows. The progress of receptor synthesis can be followed and controlled by means of suitable detection units.

As soon as the synthesis of the receptors is completed, the reaction regions are cleaned and are then available for an analyte determination method.

4.3 Nucleic Acid Analysis using Oligochips—Basic Principle

As already shown for several arrangements (for example Molecular Medicine Today, 9/97, pp. 384–389; Trends in Biotechnology, 11/97, pp. 465–468), it is possible to use the hybridization of nucleic acid strands onto a, usually short, complementary sequence, a so-called oligonucleotide or oligo, for sequence analysis. For this purpose, high-density arrangements of synthetic oligonucleotides are generated onto a solid matrix and permit multiple parallel hybridization experiments. The leading method (August 98) is a photolithographic and thus local activation of synthesis precursors. Based on the technique which has been learned from the production of microelectronics, the parallel arrangements are referred to as chips.

An enormous analytical capacity is produced by a massive increase in the number of reaction regions ("measurement points"), i.e. defined oligos at a defined site.

The sample to be investigated normally contains DNA or RNA. It may be necessary to isolate and replicate these in an amplification step (for example PCR), and moreover acquire a label, for example a dye, fluorescent or luminescent label.

Sequencing of a DNA molecule is also possible through a sufficiently large number of receptor-charged regions (reaction regions) (Sequencing-by-Hybridization SBH, see BioTec 3/98, pp. 52–58), and other applications show the determination of point mutation polymorphisms (i.e. differences between individuals in single bases in a defined DNA section) and permit, inter alia, identification of such polymorphisms in hundreds of subjects in parallel (Science 280, 5/98, pp. 1077–1082).

The investigation of whole genomes and of the gene expression status of whole cells also becomes possible for the first time (for example Proc. Nat. Acad. Sci. USA 95, 3/98, pp. 3752–3757).

The invention described herein accordingly allows the use of a large number of established methods for investigating nucleic acids and genetic material. This is simultaneously associated with a large increase in such applications and thus an enormous economic advance, because it is expected that the optofluidic microprocessor will provide such technology more flexibly than available methods and at distinctly lower costs.

4.4 Photoactivated Synthesis of Oligonucleotides and Peptides on the Support In the assembly of receptors on the support there is site-specific addition of receptor building blocks, for example single bases (G, A, C, T) or oligonucleotide sequences (preferably about 2 to 4 bases long) in the individual regions by means of photoactivation by a suitable light source. The channels are sequentially filled with the synthesis building blocks, for example G, A, C and T, and irradiated site-specifically along the channels with high-resolution light of a particular wavelength and intensity. Between the coating cycles, the channels are appropriately rinsed in order to remove unbound receptor building blocks.

This results in a large number of reaction regions (specific binding or hybridization sites) in each channel, each reaction region serving, because of its individual receptor sequence, for the binding and subsequent detection of a specific analyte, for example a DNA fragment. The reaction regions are separated from one another in one dimension of the planar support by the walls of the channels, and in the second dimension, along the individual channels, a corresponding free space is left between two adjacent reaction regions on photoactivation.

Photolithography can also be used for the photo-activated binding of the receptor building blocks. However, other methods can also be employed.

An illumination method using a programmable light source matrix, for example a self-luminous light source matrix, a light valve matrix or a reflection matrix, whose matrix points or light source elements can be deliberately controlled, in particular in relation to the intensity and, where appropriate, color of the light, is particularly preferably carried out. Thus, it is possible with such a matrix to generate in each case the required two-dimensional illumination patterns in a simple manner, in particular in a computer-assisted manner. The preferred photoactivation of the oligos for producing the support is effected directly by the illumination matrix. The wavelength necessary for this, for example 365 nm (upper UV region near to visible light), can be controlled with all variants of the programmable light source matrix.

It is also possible to assemble receptors from amino acid or/and peptide building blocks in a corresponding way.

4.5 CCD Chip Detection of the Specific Detection Reaction

As described, the binding of a DNA analyte is to lead directly or indirectly to a detectable signal, for example a light signal. This can take place, for example, by absorption, an exciting light (fluorescence) or by photon emission (luminescence). The signal is detected preferably by use of a CCD chip which is preferably placed directly underneath the support. The excitation light source is preferably placed over the support and, correspondingly, the translumination method is used for measurement. Each light signal can be detected on the CCD chip, in particular differentially according to intensity and, if required, also according to wavelength (color). The recorded spectrum can be evaluated qualitatively or quantitatively. In addition, differentiation of wavelengths and intensities also allow signal sources to be differentiated.

The types of excitation light for the detection method must be chosen to be monochromatic (for example laser light for fluorescence excitation) or heterogeneous (for example white light for absorption measurement) depending on requirements.

5. IMPROVEMENTS AND ADVANTAGES COMPARED WITH CURRENT SYSTEMS

The novel supports overcome the disadvantages, listed below, of mask-based photolithography methods or in situ spotting.

The principle of extended wetting of the entire chip surface with fluid does not permit any multiplexing in production. Thus, the number of production cycles for 20 base-long oligos increases on use of dinucleotides ($4^2$=16 possibilities) from 4×20=80 hybridization steps to 16×10=160, which means a doubling. The same also of course applies to the intermediate washing cycles.

Synthesis of the photoactivatable bases on the planar chip surface, just like the required washing steps in the production of chips, cannot be achieved except by dipping processes (chip is dipped in the liquid) which involve much space and manipulation, or rinsing processes along the surface, which involves much liquid, (for example centrifugation principle from semiconductor technology), which represents a very great impediment of miniaturization and automation from the viewpoint of equipment development.

In the subsequent DNA sequence detection, uniform distribution of the sample on the chip surface is complicated (no simple and thus reliable mixing method is possible) and a correspondingly large amount of sample fluid is necessary. The search for a rare event in the sample is impossible because adequate contact of all constituents of sample with all specific measurement points cannot be ensured.

5.1 Reduction in Production Times Through Multiplexing in the Synthesis

The essential advance of the novel supports is the possibility of drastically reducing the production times for the individual synthesis of the receptor-charged supports through appropriate multiplexing between receptor building blocks as starting materials and the channels.

For site-specific generation of a large number of different receptor sequences, for example base sequences of a particular length (for example 20 bases) on a planar surface by means of locally high-resolution photoactivation, 4 (owing to the 4 different bases) synthesis cycles are required in each plane (calculation example: 20 bases in each base sequence) of the DNA chip array. There are accordingly 4×20=80 cycles for 20 base planes. On use of dinucleotides (2 bases) on the same surface, 2 planes are produced all at once, but $4^2=16$ synthesis cycles are necessary for these 2 planes. Accordingly, 10×16=160 synthesis cycles are required for 20 planes, instead of 80 cycles, which means a doubling of the production times. On use of trinucleotides (3 bases), this effect is amplified to more than five times the number of cycles. Thus, with a single planar surface, the use of individual bases is the fastest possibility for photoactivated DNA chip production. There is no possibility of reducing the number of synthesis cycles.

The synthesis of the optofluidic support differs from this in that there is the possibility of distributing the starting materials, i.e. the bases or the different variants of dinucleotides ($4^2=16$ combinations) or trinucleotides ($4^3=64$ combinations) to various channels. This means that, at least in the lower planes near the support, only one base or one of the possible base sequences is always introduced into each channel. Depending on the specified total number of base sequences to be generated in the channels of the support, it may be that this principle must in some cases be set aside in the upper planes, i.e. more than one base or oligo must flow through one of the channels for one base, dinucleotide or trinucleotide plane. Once again, this increases the number of synthesis cycles somewhat where appropriate. However, overall, there is still a very large reduction in the production times to theoretically ¼ of the cycles with single bases, ⅛ of the cycles with dinucleotides and to 1/16 of the cycles on use of trinucleotides as starting materials for receptor synthesis (and so on for longer oligos). The number of cycles required for a specific support is individual for each support and can be stated only as a statistical average when the number of reaction regions on and in the support, the number of parallel channels and the length of the oligos to be synthesized on the support is predetermined. Optimization of the synthesis times of a support is to take place by means of a software tool to be developed (for example CAMS Computer Aided Multiplexing Synthesis) which is integrated in the control of the analytical system to be developed or in the interfaced computer.

5.2 Reduction of the Starting Materials and Quality Assurance

The use of channels very greatly reduces the amount of fluid required and, at the same time, increases the quality both in the synthesis of the support and in the subsequent detection of a sample compared with the use of a single area. Thus, the uniform wetting of channels is hydrodynamically very simple, consumes little fluid and therefore can be miniaturized and automated very easily. This applies in particular also to the need for adequate quality of the channel washing processes.

The fluid required is already reduced by 50% by the walls of the channels which, in principle, cover the space between two reaction regions in the support array. This applies both to the coating of the support during production, the synthesis of the receptors and to the "sample loading" for the analysis. A further reduction in the amounts of fluid results from the good wetting of the channel walls by a fluid flowing through and, in particular, by the effective washing processes which can, for example, be greatly improved by "cleansing" gas bubbles in the channels. On the other hand, good, statistically adequate distribution of the sample on a surface can be achieved only with a very large amount of sample.

A further advantage of the channels is that the cycle times are shorter, resulting from the smaller volumes of fluid and, associated with this, the faster chemical reactions and operations. This results in both synthesis and hybridization times being shorter.

This additionally results in a distinct reduction in errors both in production and in detection, which further increases the number of measurements which can be evaluated per usage of material and time, and forms the basis for quality assurance based on accurately definable and reproducible flow processes.

The simple miniaturization and automation of the operations in the novel supports form the basis for simple miniaturization and automation of the entire novel analytical system based on the supports.

5.3 Three-Dimensional Reaction Surfaces

It is possible by suitable design of the cross-sectional geometry of the individual channels to increase the useful reaction surface. The size of this area is just as important for the addition of the oligos during production as for the accumulation of the DNA fragments from the sample which are flowing by, and the intensity of the light signals resulting from hybridization.

Thus, a rectangular channel has, provided the height and width are identical, on use of the walls and the top surface four times the reaction surface for an identical base area, i.e. the same space requirement in the two dimensions of a planar support. Even if hydrodynamic requirements lead to the channels having a round design inside (for example possibilities of better cleaning by gas bubbles in the channel), the reaction surface is still about three times that with a planar surface. The use of this three-dimensional flow geometry makes possible to reduce further the starting material requirement (production and analysis).

Another effect can likewise be influenced by the cross-sectional geometry of the channels: the reflection of light at the transition from the interior of the channels to the surrounding medium of the support. Thus, any curvature has either a focusing or scattering effect on the direction of propagation of the light. Thus, the light paths can be optimized in the support by appropriate choice of the upper and lower sides of the flow channel geometry.

5.4 Parallel CCD Chip Detection

Measurement of the light signals of all the reaction regions of the support "all at once" makes use of the continually growing potential of the high-resolution CCD camera chips. These allow detection of all light signals for reaction or hybridization detection in a single measurement procedure. For this purpose, current color CCD chips provide about 3 000×3 000 pixels with a pixel size of about 10×10 µm on an area of 40×40 mm. The state of research is already at corresponding CCD chips with about 4 000×6 000 pixels. Signal detection takes place synchronously for all pixels in fractions of a second. This means that there is a great growth potential also for the described application of CCD chip technology, and parallel detection of $10^6$ individual reaction regions in the support is technically feasible. This avoids the time-consuming scanning procedures of conventional systems, and the pure measurement time is reduced to a minimum and becomes entirely insignificant in relation to other steps in the method.

Processing of the resulting quantities of data is possible without difficulty owing to the development in efficiency with a simultaneous fall in price of modern computer systems.

5.5 Direct Detection without Optical System

Direct detection of the light signals, without an optical system, by a CCD chip has the advantage of a considerably smaller amount of energy required by the light for error-free detection. Such an arrangement is said—investigated in a different connection—to consume only 10% of the amount of excitation light of a comparable arrangement with an optical system. In other words, the optical system consumes 90% of the light energy. The lower intensity of light greatly reduces unwanted light-scattering effects in the support surrounding the channels, as well as the possible need to cool the light source used. In addition, omission of an optical system means a great saving in space and a reduction in the production costs for the detection unit.

Complicated units for moving the support or the detection unit, as are necessary in scanners, are likewise entirely dispensed with. The predetermined dimensions of the CCD chips (several cm²) make it possible to use a very large number of parallel channels (several 100) with a moderate channel size (in the 10–100 µm range).

5.6 Disposable Supports

The supports can be designed as simple disposables (disposable chips). Possible in principle are either glass, silicon, metal, ceramic or plastic chips (cost-effective injection molding methods) and other embodiments.

The biochips of other technologies are likewise designed as disposables for a few measurements. However, in this case, the very high cost owing to the complicated production of the chips is usually not in favor of disposing of the chip after only one or a few measurements.

5.7 Flexibility of Use

The rapid and cost-effective production makes a wide variety of individual applications possible, in which, for example, oligonucleotide arrays are specifically synthesized taking account of sequence and gene databases on the Internet.

It would be possible by use of a single, multiply coiled or spiral channel to establish a hybridization in the (slow) flow-through, which also makes it possible to detect rare events (for example rarely expressed genes). This would introduce a chromato-graphic principle into DNA array technology.

The use of di-, tri- or longer oligonucleotides as synthetic building blocks makes it possible to achieve a further reduction in the production times. It is possible, especially for simpler arrays, for synthesis units to be used directly by the customer, and thus for the composition of the array to be definitively individualized.

The great flexibility of the technology is also important in view of the finding that the genes of single individuals vary greatly so that it is not possible to construct a general gene catalog for all species. The support makes it possible in this case, for example in a first measurement cycle, to match the basic data which are provided on the Internet—freely accessible or only specifically for the customers of the system—with the individual differences of a patient and, from the results, to form a corresponding second DNA array which carries out the actual tests adapted for the individual.

The achievement according to the invention can also be used to synthesize peptide sequences in the channels. This would provide highly complex and, at the same time, cost-effective peptide arrays for a large number of applications.

6. REVIEW OF SOME ASPECTS OF THE INVENTION

6.1 Support Design Variants

There is a large number of design variants both for the configuration and for the fabrication of the supports. In the arrangement of the channels in the support over the area of the detection unit it is just as conceivable to use only one channel as to arrange a large number of parallel channels. Thus, there are no technical difficulties in fabricating on an area of 25×37 mm an arrangement of 500 channels (state of the art: 500 parallel capillaries with a diameter of 900 nm) with a length of 37 mm and in each case about 750 reaction regions. The same number of reaction regions (500×750=375 000) could also be accommodated in a single serpentine channel with a length of about 20 m.

The advantage of only one channel is that the sample is presented at all measurement points of the array and is therefore particularly suitable for searching for rare constituents. A large number of parallel channels has the advantage that the production times for the support synthesis can be minimized through the multiplexing of starting materials and channels and all the flow processes. This channel arrangement is therefore to be preferred for support synthesis and all analyses with a sufficient number of copies of each analyte in the sample.

In order to benefit from both advantages in one support, it is possible to introduce the starting materials for the support synthesis by means of parallel fittings at the entry to the channels, although the channel consists of only a single, long microchannel from the sample input onward. This effect can also take place through the integration of valves in the support or the surrounding equipment components. Thus, Biacore has designed valves controlled by fluid in a two-part injection molded chip by a membrane which presses from below into the channels on the upper side of the chip and thus closes the channels.

A large number of structures and microchannel courses is possible as arrangement of the channels on the detector area. Parallel or "snake-shaped" structures, for example, are obvious for high parallelity of the fluidic processes. The division of the channels should in this case take place according to the duality principle, where two new channels arise from each channel, and all of them are of equal length. Thus, 10 divisions result in $2^{10}$=2 048 channels. Spiral arrangements have the advantage that their flow processes are less turbulent and their cleaning is better. Their great disadvantage is the feeding in and out, which must take place in the third dimension upward or downward, which is rather unfavorable in terms of fabrication techniques and optically.

A possible material for the support is, for example, glass, silicon, ceramic or metal or/and plastic. A two-layer structure is possible, and the layers can be joined together for example by gluing or bonding, or not. The structure of the channels may in this case be introduced either only into one or else into both sides or halves. Fabrication methods which can be used for this purpose are, inter alia, laser or precision milling. Injection molding is particularly cost-effective and allows adequate quality of fabrication. Other methods are the LIGA technique or hot molding.

6.2 Support Synthesis

There are in principle two possibilities for synthesizing the individual capture receptors, for example oligos, on the reaction regions in the support array. The customer purchases finished supports from the manufacturer with a predetermined selection of immobilized base sequences, or he synthesizes his own chosen sequences on unlabeled supports in a synthesis unit. Information about appropriate sequences can be found, for example, in databases on the Internet, where they are provided freely or else specifically by the support manufacturer.

6.2.1 Synthesis Unit

The synthesis unit consists of a suitable light source which irradiates site-specifically, with great accuracy and exact resolution, the reaction regions in the support array on synthesis of the receptors, for example bases or base sequences, on the support surface or the channel walls. As already mentioned under 4.4, the illumination can take place by means of a programmable light source matrix. It is also possible to use a photolithography unit like those employed in semiconductor chip production for the photoactivated etching of Si wafers.

6.2.2 Finished Support Synthesis by the Manufacturer

In the case of marketing of finished supports, the manufacturer carries out the synthesis. The latter requires for this purpose an appropriately efficient synthesis unit which uses oligos which are as long as possible (3 or more bases long) as starting materials, which are introduced (injected) in parallel into the channels, and thus minimize the synthesis times for each support (multiplexing). It is possible in this case to provide special accesses in the supports with the aim of obtaining the maximum number of parallel and thus short channels, irrespective of the channel structure provided for the analytical procedure.

6.2.3 Starting Materials in the Support

For applications where individual configuration of the arrays, but not rapid synthesis of the supports, is what matters, it is possible to provide the starting materials (G, A, C, T and buffer etc.) directly in the support in corresponding reservoirs. The excess starting materials must be collected in a corresponding chamber in the support. The volume of such a chamber can be designed without difficulty to have a multiple of the total channel volume through an expansion in the third dimension upward or downward. One conceivable application of this support variant is particularly for research laboratories, but also for small medical practices.

The principle of capillary force can in this connection be used in a possible design variant directly for fluid transport in the support. No mechanical system would be used, and the filling of the capillaries with the starting materials and the sample could take place by simply adjusting a valve in the support. The "waste chamber" could display a supporting suction effect through embedding a suitable nonwoven material. In order to minimize the required amounts of fluid, care should be taken that the capillaries are always of the same length in these one-way flow designs (no circulation and thus no reuse of the starting materials). This is likewise important for the functioning of the capillary force as pump.

A further variant is vertical alignment of the planar supports, so that gravitational forces can also be utilized for fluid transport in the support. If these forces are insufficient to achieve all the necessary fluid transports into the support, other suitable pumping mechanisms should be provided. One possibility for this is electrophoretic movement of the fluids through electrodes integrated into the support, or by reducing the volume in the chambers of the support by appropriate introduction of force from outside into the support (conventional pump).

6.2.4 Starting Materials in the Synthesis Unit

In principle, the provision of the starting materials for the support synthesis in storage containers offers the advantage of multiplexing of finished base sequences and parallel channels, which is why this design variant is advisable for (ultra)high throughput screening and support manufacturers. The multiplexing can take place at the interface to the support in which a specific base sequence wets a different channel for each synthesis cycle. A more technically elaborate but, where appropriate, more reliable method is multiplexing in the equipment through an appropriate valve system. Account must be taken here of cross-contamination, which may arise through the use of different base sequences.

Another point which must be taken into account is the collection and disposal of excess material at the exit from the individual channels. It is conceivable in this connection both to circulate (reuse the emerging material) and to dispose of the emerging starting materials.

6.3 Analyte Determination

Analysis of nucleic acid sequences takes place as with other oligonucleotide arrays by hybridization of nucleic acids in the sample material onto complementary strands among the immobilized oligonucleotides.

As another possible use of the support, is to couple peptide sequences in the channels, likewise in accordance with in situ synthesis principles. Such peptides are capable of diverse and, in some cases, highly specific binding reactions with peptides, proteins and other substances, so that the range of potential analytes can be considerably extended.

Synthesis in the support would make available for the first time very highly parallel and, at the same time, cost-effective peptide arrays for a large number of applications.

6.3.1 Analytes

Examples of analytes are nucleic acids (DNA, RNA, in specific cases also PNA). These nucleic acids can be obtained from complete genomes, fragments thereof, chromosomes, plasmids or synthetic sources (for example cDNA). In one embodiment, the sample material may originate from the human genome.

Further examples of analytes are proteins, polypeptides and peptides of all types, for example hormones, growth factors, enzymes, tumor antigens, serum factors, antibodies, carbohydrates, for example various sugars in foodstuffs or agricultural crops, functional sugars, polymers and other organic molecules, for example drugs of abuse, pharmaceuticals, metabolites, amino acids, transmitters, pesticides, insecticides, paints, various toxins etc.

6.3.2 Variants for Binding to the Immobilized Interaction Partner (Receptor)

The binding of the analyte to the receptor can in the case of nucleic acids take place by hybridization of complementary nucleic acids, for example longer molecules such as cDNA, synthetic oligonucleotides, PNA, RNA. Peptides as receptors, for example synthetic peptides or natural peptides, can bind to the analyte via protein-protein or protein-nucleic acid interactions.

6.3.3 Variants for Signal Generation

Two principles are preferably employed for signal generation, namely: direct detection of an analyte which was labeled beforehand or during the reaction (preferred method in nucleic acid analysis by means of hybridization) and indirect detection through competition of the analyte or the target sequence with a labeled standard. The first variant is well established for some applications, but tends to be rather unsuitable for diagnostics for example of serum components, which is possible with peptide arrays also in the support. The second variant is therefore to be preferred for these applications, and it moreover allows in principle, sample preparation by the user to be simpler.

Direct detection can take place by labeling the analytes with a dye for absorption measurement, a fluorescent dye, labeling the analytes with reporter enzyme, subsequent reaction (for example chemo- or bioluminescence), selective labeling of the bound analyte, for example in the case of nucleic acids by intercalating (fluorescent) dyes, double strand-binding proteins or double strand-binding antibodies or a secondary detection of the bound analyte with a second component, for example in the case of PNA-DNA hybrids by DNA-specific antibodies. Labeled standards which can be used are enzyme-coupled standards (for example chemo- and bioluminescence with alkaline phosphatase, peroxidase etc.) or (fluorescence) dye-coupled standards. Protein standards can be employed as fusion proteins with a reporter enzyme (see above) or an autofluorescent protein (for example GFP), for example for recombinant antibodies, protein hormones, growth factors etc.

6.4 Provision of the Sample Material

There are likewise various design variants for the provision of the sample material. The nature of the provision is irrelevant to the actual detection because it is always necessary to provide a sufficient amount of in liquid dissolved DNA fragments at the interface for the desired investigation.

6.4.1 External Sample Preparation

The sample preparation can take place either manually in the laboratory, in a separate analysis system or in a preparation unit integrated into the same system. The sample ready for detection is then introduced into the support by means of manual or automatic pipetting or comparable methods.

6.4.2 Sample Preparation in the Same Support All in One

Precisely when multiplexing is used to reduce the production times in the support synthesis it is possible to achieve identical or even shorter times for the receptor synthesis than would be necessary, for example, for DNA amplification of the sample by PCR. This makes it worthwhile to integrate a PCR into the synthesis system or even into the support for many applications.

Besides the time-consuming PCR, it is also possible to integrate the preceding cell disruption, for example via readily automatable methods such as ultrasound or high voltage, just like the DNA isolation.

6.5 Detection Unit

The reading of the light signals for the detection reactions in the support array is to take place in a detection unit where the excitation light source (fluorescence, luminescence or absorption as optical detection) is arranged directly opposite to the CCD chip for light signal measurement. The support array is located between light source and detection chip (sandwich architecture). An illumination matrix can be used as excitation light source. The spatial arrangement of this unit may depend on requirements (for example use of gravitation for flow processes in the chip). This maximally compact architecture minimizes the paths traveled by the light and thus also the intensity of light required. It is intended to dispense with the use of an elaborate, light-consuming and costly optical system which occupies much space, both on the excitation side and on the detection side.

6.5.1 Temperature During the Hybridization

The temperature control (at present typically 60° C.—most recent developments also now make hybridization possible at 25° C. with low-salt conditions) during the hybridization can take place either by appropriate temperature elements in the detection unit or by the excitation light source or the excitation light per se. Temperature elements in the supports are likewise possible.

6.5.2 Excitation Light Source

Suitable light sources are, depending on the analyte markers (detection method via absorption or fluorescence etc.), highly parallel light from a lamp (white light), highly parallel light from a flash tube, highly parallel monochromatic light, a monochromatic streak of laser light, extensive illumination through widening of the laser beam, a monochromatic laser beam or a programmable light source matrix.

An appropriate optical grating or an appropriate optical system can, where appropriate, be provided between excitation light source and support array.

6.5.3 CCD Camera Detection

The detection unit preferably consists of only one CCD chip. These currently have about 2 000×3 000 pixels on an area of, for example, 25×37 mm (Cannon). Arrangement of about 500 parallel channels with a diameter of about 20 μm (every second double pixel row) on such an area of 25×37 mm results in 750 measurement points (fields) in each channel if only every second double pixel is used under the channel. This would provide 375 000 reaction regions on a single support, each reaction region covering 4 colored and 12 black and white pixels and having an area of 20×20 µm. The light signals must be generated with maximum density on the optical CCD chip so that faulty assignment of light signals and measurement points with their specific base sequence, and overlap of adjacent light signals, can be precluded. Otherwise, serial detection of overlapping regions is possible, or fiber optic elements are employed.

The resulting large number of measurements (4×500× 750=1.5 million colored signals or 4.5 million intensities between 0 and 4 096 digital values) which are available (current CCD chip state of the art) form the basis permitting extensive statistics in the analysis of the detected light signals. The processing of the resulting quantities of data is possible without difficulty through the development in efficiency with, at the same time, fall in price of modern computer systems.

The detection of the detection reaction can provide both qualitative and quantitative information, in particular which capture molecules (position in the array) have found binding partners (evaluation of the, for example, fluorescent label) and how many capture molecules in a class have found a hybridization partner.

It is possible where appropriate to provide an appropriate optical grating or an appropriate optical system between the support array and the CCD camera.

If detection with a CCD camera or a CCD chip does not provide adequate signals, detection in the analytical system is also possible by other, more sensitive sensors.

Of interest in connection with the present invention is the use of an inspection unit as described in the German patent application 198 39254.0. This inspection unit comprises an electronically controllable light source matrix and a light sensor matrix which is located opposite to and faces the light source matrix, namely CCD image recorder.

It is conceivable in this connection that the user produces his supports himself and uses them directly. He simply downloads the required data (DNA sequences) from a CD-ROM or from the Internet and produces in his illumination matrix-CCD unit his individual DNA chip, then wets it with the sample and reads the signals.

If, for example, every second pixel in this arrangement is measured for the photoactivation, it is possible to use the pixels in between, which lie in projection inside a channel, for a permanent process control. Thus, for example, it is possible of individual and dynamic following of the flowing in of a gas bubble between two fluids in a channel. It would also be conceivable to color the carrier fluids for G, A, C and T, so that the presence of the correct oligos could be checked and a color change might signal a cross-contamination. In the subsequent detection there could in turn be site-specific and, if necessary, even color-specific light excitation. This results in entirely novel possibilities for detection method nods currently not available as yet.

Using the inspection unit (illumination matrix-CCD unit), it is possible to monitor the flow processes in the channels in a support both during the production—i.e. in the oligo synthesis—and during the analysis. For this purpose it is possible to use, for example, cleansing gas bubbles between two fluids in the channels or a coloring of the individual fluids.

It is possible to use an illumination matrix which generates and transmits the necessary wavelength of, for example, 360–370 nm, for photoinduced elimination of protective groups during the synthesis of DNA oligos on or in the support.

Detection of the detection reaction in the support can likewise take place in the inspection unit. If the detection is achieved via fluorescent markers, it would be necessary, where appropriate, to change the background illumination (automatically possible). For this purpose it would be possible to use optical filters or/and glass fiber elements (tapers). Where appropriate novel detection methods are also used which is made possible only by the extremely flexible, individual irradiation and detection of the individual reaction region.

A temperature of about 55–65° C. is required for standard hybridization of DNA, RNA and PNA strands with one another. In the simplest case, this temperature can be generated by the energy emitted by the illumination matrix (waste heat and wavelength). This would allow the arrangement to be made more compact.

8. EXEMPLARY EMBODIMENTS

The synthesis of DNA molecules in channels can take place with use of standard synthons, for example phosphoramidite building blocks, with suitable protective groups, for example dimethoxytrityl (DMT). A corresponding fluidic DNA synthesis can take place starting from a linker coupled to the solid phase.

This format can be combined for the preferred embodiment of the invention with a light-dependent control of the DNA synthesis. For this purpose, protective groups which permit light-dependent deprotection are known, so that the protective group, which is usually linked on the 5' carbon atom of the synthon, is eliminated by light of suitable wavelength. The synthesis of nucleic acids with a length of 18 or more nucleotides is possible in capillaries in this way.

The reaction products can be analyzed, for example by high performance liquid chromatography (HPLC), by detaching the synthesized DNA oligomer, as is possible on use of suitable linkers. In this case it is possible to show the efficiency of the capillary DNA synthesis via the proportion of full-length products.

For light-dependent DNA synthesis, the reaction region on the support is illuminated site- or/and time-specifically with a suitable light source, for example with a mercury vapor lamp, laser light (for example 373 nm nitrogen laser) or with a UV LED. Other light sources which have sufficiently high-energy radiation are likewise suitable too.

Figure 1:
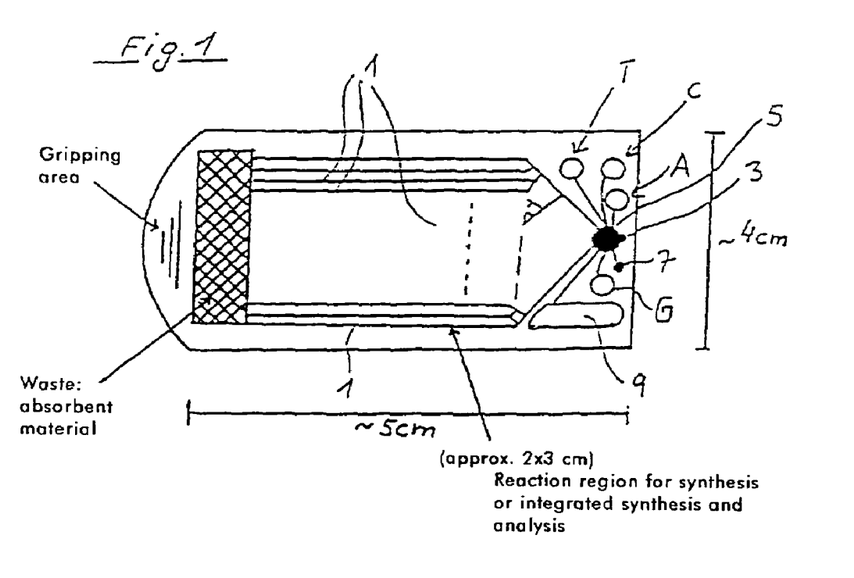
FIG. 1 shows a highly schematic plan view of a support according to the invention.

FIG. 1 shows a transparent support in a plan view in a highly schematic manner. The channels 1 which run parallel to one another are evident, for example 500 channels with a length of 37 nm. T, G, A, C in FIG. 1 designate reservoirs for the individual starting materials (bases). 3 designates the gas inlet. 5 identifies a valve. 7 identifies the sample input, and 9 designates an entry for further synthetic chemicals and cleaning/washing liquid.

Figure 2:
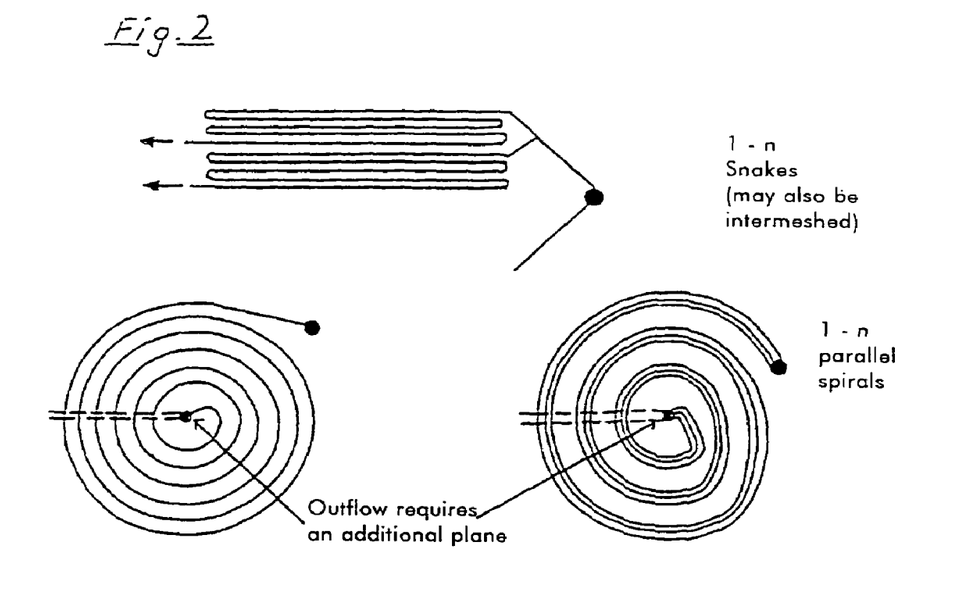
FIG. 2 shows examples of channel arrangements in a support according to the invention.

FIG. 2 is a diagrammatic depiction of other examples of alternative channel arrangements.

Figure 3:
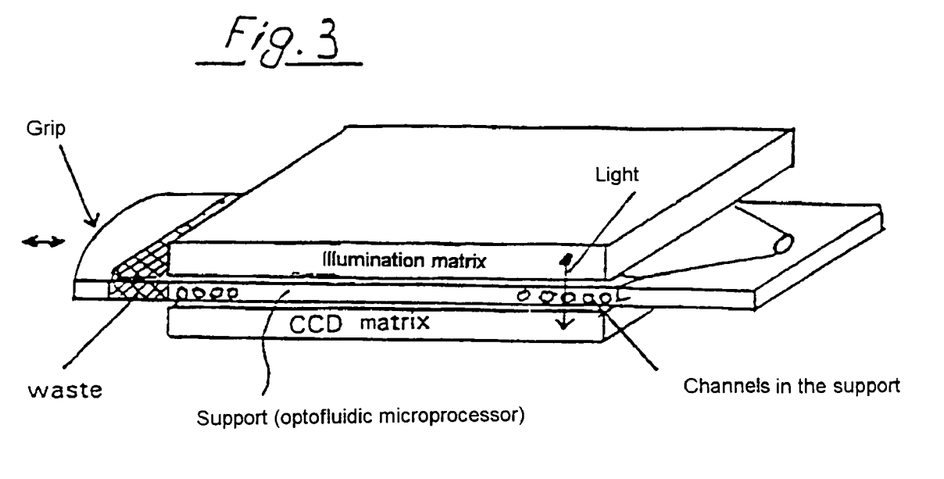
FIG. 3 shows a diagrammatic depiction of a support in an inspection unit composed of programmable light source matrix and CCD matrix.

FIG. 3 shows the support of FIG. 1 in an inspection unit composed of programmable light source matrix, for example an LCD matrix, and a CCD detection matrix.

Figure 4:
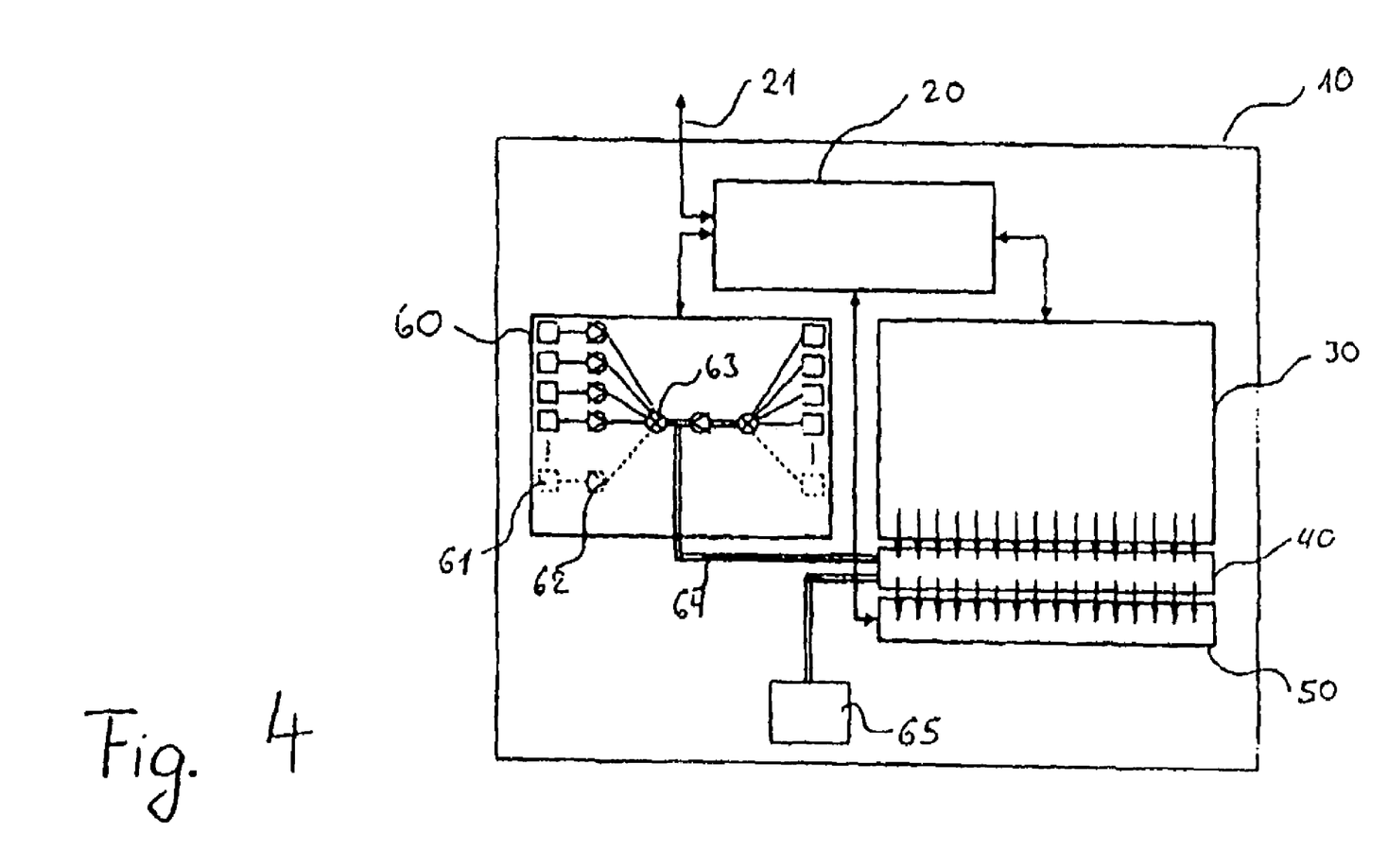
FIG. 4 shows a diagrammatic depiction of an apparatus of the invention for a lightassisted integrated synthesis and analysis method and FIG. 5 shows the structure from FIG. 4 for a fluidic individualization of reaction regions.

FIG. 4 depicts an apparatus of the invention with an exchangeable support 40, the structure in principle depending on whether the support is changed in each cycle or only when worn. In the latter case there is cleaning and subsequent reuse of the same channels. A programmable light source matrix 30 is depicted. Its programmability can be integrated into the system component 20, which consists of a calculator or a computer, so that only one freely controllable light source matrix is necessary as component 30. This light source matrix 30 beams light of defined wavelength and intensity onto any addressable sites of an at least two-dimensional matrix which serves for highly parallel illumination of the reaction regions in the support 40. Said support 40 is irradiated individually by the light source matrix 30 with the compute-r-controlled light pattern consisting of energy waves in all reaction regions. Fluids provided by the fluidics module 60 are transported via the fluidic connection system 64 into the support 40 and conveyed further in its microstructure, which is not depicted in the drawing, in a suitable manner to the reaction regions. The support 40 becomes an optofluidic microprocessor in this way. The latter can be either changed after each use or cleaned after each use and changed only for servicing purposes when worn.

The entering light can be used, for example, for absorption measurements, to activate photoreactions or to excite fluorescence.

The light emerging from the support 40 or from the optofluidic microprocessor can, for example, be the light from the light source matrix 30 transmitted through the support. It can, however, in this case also comprise light signals which are generated in the individual reaction regions of the support 40 by, for example, fluorescence or luminescence.

The detector matrix 50, which consists for example of a CCD chip with or without optical system, is arranged in relation to a light source matrix 30, with a support 40 being located in between, so that the result is a triple matrix arrangement composed of light matrix, support and detector matrix.

The fluidic module 60 serves to supply the reaction support 40 for example with starting materials, protective gases, chemicals such as solvents etc., and sample material. The fluidic module 60 consists of tanks 61 which are emptied in a suitable manner by pumps 62 and valves 63. The tanks can be exchanged or refilled singly or in a cluster. Fluids which are required permanently, such as, for example, protective gas, can also be supplied continuously by means of lines (without tanks in the system). The fluidic waste from the various methods can be collected either in tanks integrated in the support 40 or in a waste system 65 or, in the case of clusters, outside the individual system.

The system boundary 10 of the apparatus, which can be employed as a single device or else in central or decentral clusters, is likewise depicted. There is always information technology linkage between these clusters. The systems located at a site may also be supplied together, by manual operation or automated components, with energy, fluids such as starting materials, reaction chemicals, protective gases and sample material, and with the required supports.

The system component 20 in the form of a computer or calculator undertakes the control of the system. This includes the control, on the basis of the calculation of the probe or receptor sequences for the individual reaction regions, of the light source matrix 30 and of the fluidic component 60. The data from the detector matrix 50 are moreover collected and evaluated.

Each apparatus can thus communicate beyond its system boundary 10 with other apparatuses or systems consisting in turn of an apparatus of the invention or other computers or databases. This can take place, for example, via lines, bus systems or via the Internet. It is moreover possible for communication to take place with central coordination by a master computer or as cluster of equal-access systems. A data interface 21 to the system environment is likewise provided.

Figure 5:
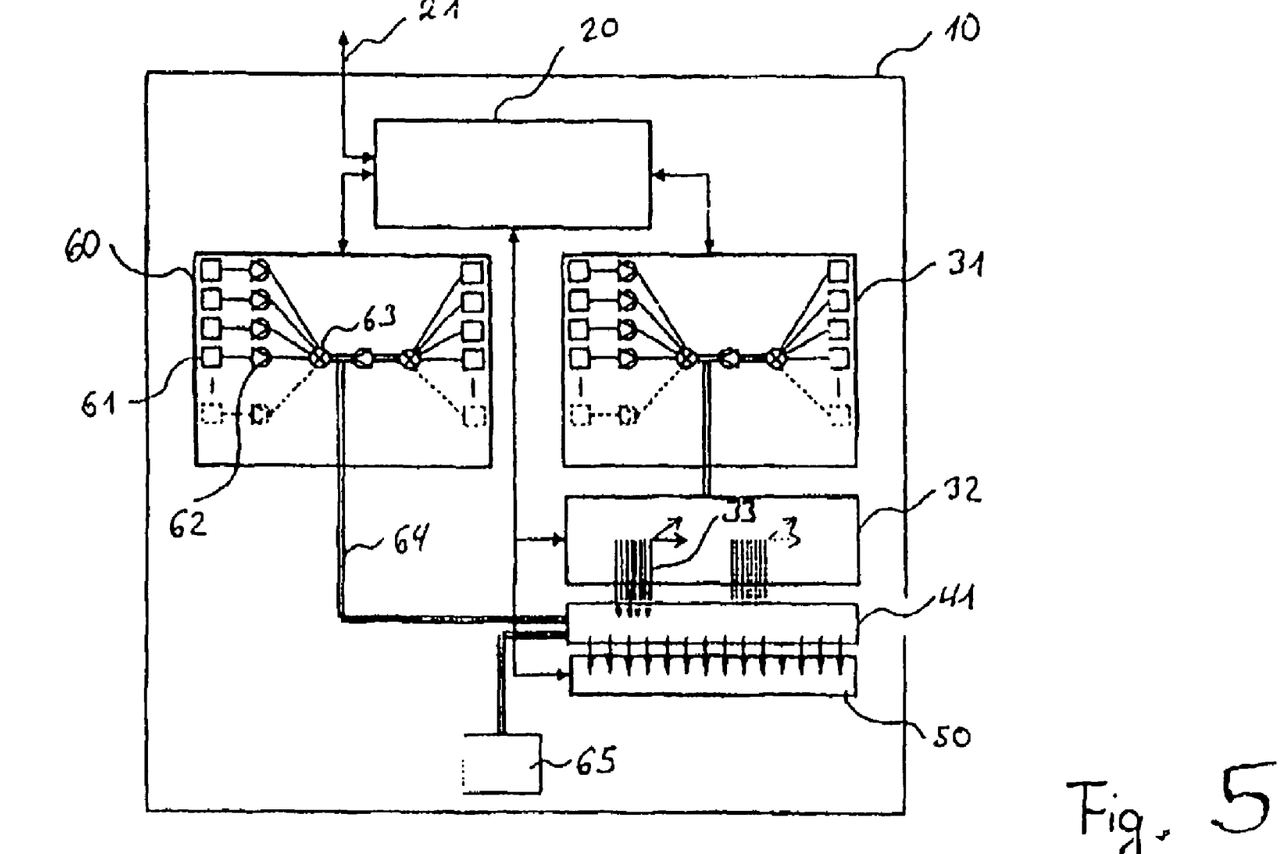

FIG. 5 shows the structure from FIG. 4 for a fluidic individualization of the reaction regions. A support 41 is depicted once again. This is utilized individually under computer control by the fluidic deprotection module 32. The fluids provided by the fluidic module 60 are transported via the fluidic connection system 64 into the support and, in its microstructure which is not depicted in the drawing, conveyed further in a suitable manner to the reaction regions. This makes the support 41 into an optofluidic microprocessor. The latter can be either changed after each use or cleaned after each use and changed only for servicing purposes when worn.

It is possible to feed light into this support for example from above or/and from the side to excite fluorescence reactions etc.

The light emerging from the support or the optofluidic microprocessor can be generated, for example, by luminescence on the reaction regions.

The fluidic deprotection module 32 is able to bring each reaction region on the support 41 into contact individually with fluids by use of at least one of the wetting components 33 (for example nozzles, capillaries etc.). It is possible in this way to activate, for example, local chemical and biochemical reactions.

The fluidic module 31 serves to supply the fluidic deprotection module 32 with starting materials or chemicals. The fluidic module 31 has a comparable structure to the module 60 and consists, depending on requirements, of tanks, lines, valves etc.

The detector matrix 50, which consists for example of a CCD chip with or without optical system, is arranged in relation to a fluidic deprotection module 32, with a support 41 located in between, in such a way that once again a triple matrix arrangement is produced thereby.

The fluidic module 60 serves to supply the support 41 for example with starting materials, protective gases, chemicals such as solvents etc., and sample material. The fluidic module 60 consists of tanks 61 which are emptied in a suitable manner by pumps 62 and valves 63. The tanks can be exchanged or refilled singly or in a cluster. Fluids which are required permanently, such as, for example, protective gas, can also be supplied continuously by means of lines (without tanks in the system). The fluidic waste from the various methods can be collected either in tanks integrated in the support 41 or in a waste system 65 or, in the case of clusters, outside the individual system.

The system boundary 10, which has already been explained, of the apparatus and the system component 20 in the form of a computer or calculator, which undertakes the control of the system, is depicted once again. This includes the control of the fluidic modules 31 and 60, and of the fluidic deprotection module 32, on the basis of the calculation of the probe sequences for the individual reaction regions. The data from the detector matrix 50 are moreover collected and evaluated.

Each apparatus can thus communicate beyond its system boundary 10 with other apparatuses or systems consisting in turn of an apparatus of the invention or other computers or databases. This can take place, for example, via lines, bus systems or via the Internet. It is moreover possible for communication to take place with central coordination by a master computer or as cluster of equal-access systems. A data interface 21 to the system environment is likewise provided.

What is claimed is:

1. A method for producing a support containing polymeric receptors for determining analytes, comprising the steps of
    (a) providing a support, wherein said support comprises a support body comprising at least one channel which comprises a conduit with a top, a bottom and two sides having an inlet and an outlet for passing fluid from the inlet to the outlet, and at least one reaction position in the support body, wherein said support is optically transparent at least in the region of said at least one reaction position,
    (b) placing said support body between a programmable light source matrix and a detector matrix,
    (c) passing liquid with building blocks for synthesizing said polymeric receptors through the channel or channels of the support body,
    (d) site- and/or time-specifically immobilizing the said building blocks on predetermined reaction positions in the channel or channels by illumination of said predetermined reaction positions by said programmable light source matrix, wherein the illumination position of said light source matrix is monitored by computer using said detector matrix, and
    (e) repeating steps (c) and (d) until said polymeric receptors have been synthesized on the predetermined positions.

2. The method as claimed in claim 1, wherein said method produces a support which comprises defined areas, each of which contains identical receptor species.

3. The method as claimed in claim 1 wherein said channels are arranged on the surface of said support.

4. The method as claimed in claim 1 wherein said support comprises several hundred channels per support body and said channels are arranged parallel to one another.

5. The method as claimed in claim 1 wherein said polymeric receptors are selected from the group consisting of nucleic acids and nucleic acid analogs.

6. The method as claimed in claim 5, wherein said building blocks are selected from the group consisting of nucleotides, oligonucleotides, nucleotide analogs and oligonucleotide analogs.

7. The method as claimed in claim 1 characterized in that the illumination takes place via a programmable light source matrix.

8. The method as claimed in claim 1 characterized in that the pattern of polymeric receptors is determined by computer programming.

9. The method as claimed in claim 1, wherein said at least one channel is a capillary channel.

10. The method as claimed in claim 1, wherein said at least one channel contains a plurality of said polymeric receptors.

11. The method as claimed in claim 1, wherein said at least one channel provides a three dimensional surface area for synthesis of said polymeric receptors.

* * * * *